(12) United States Patent
Liu

(10) Patent No.: US 9,913,124 B2
(45) Date of Patent: Mar. 6, 2018

(54) METHOD AND SYSTEM FOR SEARCHING FOR ELECTRONIC CIGARETTE OF SAME TYPE

(71) Applicant: KIMREE HI-TECH INC., Road Town, Tortola (VG)

(72) Inventor: Qiuming Liu, Shenzhen (CN)

(73) Assignee: HUIZHOU KIMREE TECHNOLOGY CO., LTD. SHENZHEN BRANCH, Shenzhen (CN)

( * ) Notice: Subject to any disclaimer, the term of this patent is extended or adjusted under 35 U.S.C. 154(b) by 0 days.

(21) Appl. No.: 15/306,450

(22) PCT Filed: Apr. 24, 2014

(86) PCT No.: PCT/CN2014/076151
§ 371 (c)(1),
(2) Date: Oct. 24, 2016

(87) PCT Pub. No.: WO2015/161492
PCT Pub. Date: Oct. 29, 2015

(65) Prior Publication Data
US 2017/0048691 A1  Feb. 16, 2017

(51) Int. Cl.
*H04L 12/16* (2006.01)
*H04W 4/16* (2009.01)
(Continued)

(52) U.S. Cl.
CPC ............ *H04W 8/005* (2013.01); *A24F 47/00* (2013.01); *A24F 47/008* (2013.01); *G08B 6/00* (2013.01);
(Continued)

(58) Field of Classification Search
CPC ....... H04W 8/005; H04W 4/008; H04W 4/16; H04W 76/023; H04W 76/027;
(Continued)

(56) References Cited

U.S. PATENT DOCUMENTS 9,270,782 B2 * 2/2016 Hala ........................ H04L 67/34
9,638,537 B2 * 5/2017 Abramson ......... G01C 21/3626
(Continued)

FOREIGN PATENT DOCUMENTS

CN  102940313 A  2/2013
CN  103653261 A  3/2014
(Continued)

OTHER PUBLICATIONS

International Search Report (ISR) issued by the State Intellectual Property Office of the Peoples Republic of China dated Jan. 26, 2015 for PCT/CN2014/076151, China.

*Primary Examiner* — Pablo Tran
(74) *Attorney, Agent, or Firm* — Tim Tingkang Xia, Esq.; Locke Lord LLP

(57) ABSTRACT

A method and system for searching for an electronic cigarette of a same type, the method comprises at least two electronic cigarettes performing a communication connection. The method comprises the following steps: S1, at least one electronic cigarette sends broadcast information carrying a type of the electronic cigarette to another electronic cigarette within a preset range; S2, the another electronic cigarette receiving the broadcast information determines whether the type carried by the broadcast information is the same as the another electronic cigarette's type, and performs a vibration alert if the type same. Via the present method, it can be quickly known whether an electronic cigarette user having a same electronic cigarette is present in the surroundings, and an enthusiast of an electronic cigarette of a same type can be found, enabling an electronic cigarette to no (Continued)

longer be an individual, and thereby improving user experience.

13 Claims, 6 Drawing Sheets

(51) Int. Cl.
    *H04W 4/00*         (2009.01)
    *H04W 8/00*         (2009.01)
    *A24F 47/00*       (2006.01)
    *G08B 6/00*        (2006.01)
    *A61M 15/06*      (2006.01)
    *H04W 4/06*        (2009.01)
    *H04W 4/08*        (2009.01)

(52) U.S. Cl.
    CPC .............. *A61M 15/06* (2013.01); *H04W 4/008* (2013.01); *H04W 4/06* (2013.01); *H04W 4/08* (2013.01)

(58) Field of Classification Search
    CPC ...... H04W 76/02; A24F 47/00; A24F 47/008; G08B 6/00; H04L 12/16
    See application file for complete search history.

(56) References Cited

U.S. PATENT DOCUMENTS

| | | | |
|---|---|---|---|
| 2012/0052807 A1* | 3/2012 | Rathi | ................. H04W 76/025 455/41.3 |
| 2013/0152954 A1 | 6/2013 | Youn | |
| 2014/0092781 A1* | 4/2014 | Tan | ......................... H04W 4/16 370/259 |

FOREIGN PATENT DOCUMENTS

| | | | | |
|---|---|---|---|---|
| CN | 103716901 A | 4/2014 | | |
| KR | 101300381 B1 | 8/2013 | | |
| WO | WO 2015161486 A1 * | 10/2015 | ............. | A24F 47/00 |
| WO | WO 2015161492 A1 * | 10/2015 | ............. | A24F 47/00 |
| WO | WO 2016008096 A1 * | 1/2016 | ............. | A24F 47/00 |
| WO | WO 2016019549 A1 * | 2/2016 | ............. | A24F 47/00 |
| WO | WO 2016029429 A1 * | 3/2016 | ............. | A24F 47/00 |

\* cited by examiner

METHOD AND SYSTEM FOR SEARCHING FOR ELECTRONIC CIGARETTE OF SAME TYPE

TECHNICAL FIELD

The present invention relates to daily electronic products, and more particularly relates to a method and a system for searching for an electronic cigarette of a same type.

BACKGROUND

An electronic cigarette comprises a battery component and an atomization component, it utilizes smoke liquid to be heated to atomize, and provides smokers with a substitute for cigarettes to quit smoking.

Current electronic cigarettes can substitute cigarettes to meet the users' smoking demands, but most electronic cigarettes are only independent individuals, they are provided with single function and are not provided with the function of information communication. For example, they cannot search around whether there are enthusiasts of same types of the electronic cigarettes, users' experiences are poor. As they are not provided with the function of searching the same types of electronic cigarettes, when users want to look for the same types of electronic cigarettes, there are no effective methods to quickly know information that how many electronic cigarettes around are the same with their own electronic cigarettes, and users cannot introduce relevant information to other smokers, the function of sharing information cannot be realized, thus it is harmful to popularize the electronic cigarettes and to quit smoking.

Therefore, there are defects in prior art, which need to be improved.

SUMMARY

The technical problem that the present invention will solve is, aiming at the above-mentioned defect that the electronic cigarettes in prior art cannot search around whether there are same type of electronic cigarette enthusiasts, providing a method and a system for searching for an electronic cigarette of a same type.

The technical solution that the present invention applies to solve the technical problem is: construct a method for searching for an electronic cigarette of a same type, the method comprises at least two electronic cigarettes performing a communication connection, wherein the method comprises the following steps:

S1: at least one electronic cigarette sends broadcast information carrying a type of the electronic cigarette to another electronic cigarette within a preset range;

S2: the another electronic cigarette receiving the broadcast information determines whether the type carried by the broadcast information is the same as the another electronic cigarette's type, and performs a vibration alert if the type carried by the broadcast information is the same as the another electronic cigarette's type.

In the method for searching for an electronic cigarette of a same type of the present invention, the method further comprises a step after the step S2:

S21: the another electronic cigarette performs statistics for the broadcast information carrying the type which is same as the another electronic cigarette's type, and indicates a statistics result.

In the method for searching for an electronic cigarette of a same type of the present invention, the statistics result comprises: a quantity of received broadcast information carrying the type which is same as the another electronic cigarette's type, the vibration alert comprises: a motor vibrates several times, there is a time interval between two adjacent vibrations, a number of vibration times of every vibration is same as the quantity.

In the method for searching for an electronic cigarette of a same type of the present invention, each of the at least two electronic cigarettes comprises a record table for recording electronic cigarette ID;

the broadcast information sent by the at least one electronic cigarette in the step S1 further carries its own electronic cigarette ID configured to identify the at least one electronic cigarette;

in the step S2, if the type carried by the broadcast information is determined to be the same as the another electronic cigarette's type, the another electronic cigarette firstly inquires whether the electronic cigarette ID carried by the broadcast information is in its record table, if not, writes the electronic cigarette ID carried by the broadcast information into the record table, and performs the vibration alert, otherwise, performs no response.

In the method for searching for an electronic cigarette of a same type of the present invention, the method comprises following trigger step S01 before sending the broadcast information in the step S1:

S01: each of the at least two electronic cigarettes is triggered to produce a first trigger signal of activating a sending broadcast information function.

In the method for searching for an electronic cigarette of a same type of the present invention, in the step S01, each of the at least two electronic cigarettes produces the first trigger signal of activating the sending broadcast information function when each of the at least two electronic cigarettes detects its own smoking signal.

In the method for searching for an electronic cigarette of a same type of the present invention, the method comprises a following trigger step S02 before sending the broadcast information in the step S1:

S02: each of the at least two electronic cigarettes is triggered to produce a second trigger signal of activating a receiving broadcast information function.

In the method for searching for an electronic cigarette of a same type of the present invention, in the step S2, if the type carried by the broadcast information is determined to be same as the another electronic cigarette's type, then the another electronic cigarette performs the vibration alert, at same time the method further comprises:

S3: the another electronic cigarette sends response information to the at least one electronic cigarette that sends the broadcast information correspondingly;

S4: the at least one electronic cigarette receives the response information and performs a vibration alert.

In the method for searching for an electronic cigarette of a same type of the present invention, after the step S4, the method further comprises:

S41: the at least one electronic cigarette that receives the response information performs statistics for the response information, and indicates a statistics result.

In the method for searching for an electronic cigarette of a same type of the present invention, the electronic cigarette type belongs to one or more following classifications: a brand model, a smoke liquid taste, an electronic cigarette manufacturer.

In the method for searching for an electronic cigarette of a same type of the present invention, before the step S1, the method further comprises:

S0: each of the at least two electronic cigarettes selects a classification to which its own electronic cigarette type belongs.

In the method for searching for an electronic cigarette of a same type of the present invention, in the step S0, each of the at least two electronic cigarettes selects at least two classifications to which its own electronic cigarette type belongs;

in the step S2, the another electronic cigarette performing the vibration alert comprises: vibrates times corresponding to a number of the same classifications to which the type belongs.

In the method for searching for an electronic cigarette of a same type of the present invention, in the step S21, indicating the statistics result comprises: a text display or/and a voice announcement.

The present invention further provides a method for searching for an electronic cigarette of a same type, the method comprises at least two electronic cigarettes performing a communication connection, wherein each of the at least two electronic cigarettes comprises: a control module, a wireless communication module, a vibration alert module, a prompt module, a first switch, and a second switch; the wireless communication module, the vibration alert module, the prompt module, the first switch and the second switch are connected to the control module respectively;

the control module comprises a processor, the vibration alert module comprises a motor and a driving circuit, the processor stores a record table for recording electronic cigarette ID;

the first switch is configured for simultaneously sending a first trigger signal and a second trigger signal, and the second switch is configured for sending a second trigger signal; the first trigger signal is configured for activating a sending broadcast information function, the second trigger signal is configured for activating a receiving broadcast information function;

the method comprises following steps:

S0: the each of the at least two electronic cigarettes selects a classification to which its own electronic cigarette type belongs;

the electronic cigarette type belongs to one or more following classifications: a brand model, a smoke liquid taste, an electronic cigarette manufacturer;

S01: the first switch of the electronic cigarette is triggered to generate the first trigger signal;

S1: the wireless communication module of the at least one electronic cigarette in the step S01 sends broadcast information carrying electronic cigarette ID for identifying its own electronic cigarette and a type of the at least one electronic cigarette type to another electronic cigarette in a preset range;

S02: the first switch or the second switch of the another electronic cigarette is triggered to generate the second trigger signal;

S2: the wireless communication module of the another electronic cigarette receiving the broadcast information in the step S02 sends the broadcast information to the processor, the processor determines whether the type carried by the broadcast information is the same as the another electronic cigarette's type, and if the type carried by the broadcast information is the same as the another electronic cigarette's type, firstly inquires whether the electronic cigarette ID carried by the broadcast information exists in its record table, if not, writes the electronic cigarette ID carried by the broadcast information into the record table, and controls the driving circuit to drive the motor to perform a vibration alert, otherwise, performs no response;

S21: the processor of the another electronic cigarette receiving the broadcast information performs statistics for the broadcast information carrying the electronic cigarette type which is the same as the another electronic cigarette's type, and carries out a text display and/or a voice announcement via the prompt module; a statistics result comprises: a quantity of the broadcast information carrying the type which is the same as the another electronic cigarette's type;

the controlling the driving circuit to drive the motor to perform the vibration alert comprises: the driving circuit drives the motor to vibrate several times, there is a time interval between two adjacent vibrations, a number of vibration times of each vibration alert is same as the quantity.

The present invention further provides a system for searching for an electronic cigarette of a same type, the system comprises two electronic cigarettes, each of the at least two electronic cigarettes comprises:

a control module, a wireless communication module, a vibration alert module, a prompt module, a first switch, and a second switch; the wireless communication module, the vibration alert module, the prompt module, the first switch and the second switch are connected to the control module respectively;

the control module comprises a processor, the vibration alert module comprises a motor and a driving circuit, the processor stores a record table for recording electronic cigarette ID;

the first switch is configured for simultaneously sending a first trigger signal and a second trigger signal, and the second switch is configured for sending a second trigger signal; the first trigger signal is configured for activating a sending broadcast information function, the second trigger signal is configured for activating a receiving broadcast information function;

the control module of at least one electronic cigarette is configured to load information of an type of the at least one electronic cigarette into the wireless communication module of the at least one electronic cigarette after receiving the first trigger signal;

the wireless communication module of the at least one electronic cigarette is configured to send broadcast information carrying the type of the at least one electronic cigarette to another electronic cigarette within a preset range; the wireless communication module of the at least one electronic cigarette is further configured to receive at least one broadcast information sent by the another electronic cigarette and to send the received broadcast information to the control module of the at least one electronic cigarette;

the control module of the at least one electronic cigarette is further configured to obtain the received broadcast information from the wireless communication module of the at least one electronic cigarette after receiving the second trigger signal, and to determine whether another electronic cigarette type carried by the received broadcast information is the same as the type of the at least one electronic cigarette, if the another electronic cigarette type carried by the received broadcast information is the same as the type of the at least one electronic cigarette, then to control the vibration alert module to perform a vibration alert; the control module of the at least one electronic cigarette is also configured to perform statistics for the received broadcast information carrying the another electronic cigarette type which is same as the type of the at least one electronic cigarette;

the prompt module is configured to prompt a statistics result.

The beneficial effects of implementing the method and the system for searching for an electronic cigarette of same type of the present invention are: each electronic cigarette of the present invention can send the broadcast information carrying the electronic cigarette's own electronic cigarette type to the other electronic cigarettes in the preset range, after the electronic cigarette receives at least one piece of the broadcast information, it is determined whether the type of the electronic cigarette carried by the broadcast information is the same as the electronic cigarette's own electronic cigarette type, if the type of the electronic cigarette carried by the broadcast information is the same as the electronic cigarette's own electronic cigarette type, then it is determined there are same type electronic cigarette enthusiasts around, so the electronic cigarette receiving the broadcast information can control to perform a vibration alert, and quickly learn whether there are electronic cigarette users around that use the same electronic cigarette to find the same type electronic cigarette enthusiasts, making electronic cigarettes is no longer a separate individual, to enhance the user experience, so that users know more about what type of electronic cigarette is better, which will promote the popularization of electronic cigarettes, and further facilitate quitting smoking, in order to achieve universal health of smoking.

BRIEF DESCRIPTION OF THE DRAWINGS

The present invention will be further described with reference to the accompanying drawings and embodiments in the following, in the drawings.

DETAILED DESCRIPTION OF THE PREFERRED EMBODIMENT

In order to solve the defect that the prior art cannot search for the existence of enthusiasts of a same type of an electronic cigarette around, the present invention provides a method and a system for searching for an electronic cigarette of a same type. Each electronic cigarette of the present invention can send the broadcast information carrying the electronic cigarette's own electronic cigarette type to another electronic cigarette in the preset range, after receiving at least one piece of the broadcast information, the another electronic cigarette determines whether the electronic cigarette type carried by the broadcast information is the same as the another electronic cigarette's own electronic cigarette type, if the type of the electronic cigarette carried by the broadcast information is the same as the another electronic cigarette's own electronic cigarette type, then it is determined there are enthusiasts of the same type electronic cigarette around, then the electronic cigarette receiving the broadcast information can be controlled to perform a vibration alert.

In order to better understand the technical features, purpose and effect of the present invention, the preferred embodiment will be described in detail in the following.

Figure 1:
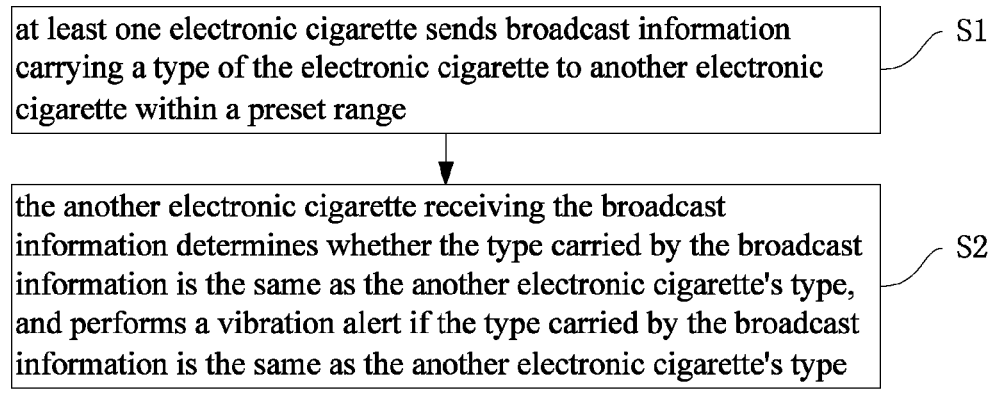
FIG. 1 is a flow chart of a first embodiment of the method for searching for an electronic cigarette of the same type of the present invention.

FIG. 1 is a flow chart of a first embodiment of the method for searching for an electronic cigarette of the same type of the present invention;

In the first embodiment, the method comprises the following steps:

S1, at least one electronic cigarette sends broadcast information carrying the electronic cigarette's own electronic cigarette type to another electronic cigarette within a preset range;

S2, the another electronic cigarette receiving the broadcast information determines whether the electronic cigarette type carried by the broadcast information is the same as the another electronic cigarette's own electronic cigarette type, and if the electronic cigarette type carried by the broadcast information is the same as the another electronic cigarette's own electronic cigarette type, perform a vibration alert.

The electronic cigarette type belongs to any of the following classifications: a brand model, a smoke liquid taste, an electronic cigarette manufacturer. Certainly they are not limited to the above three types of categories. The electronic cigarette pre-stored a code table that represents its own electronic cigarette type, there are code segments that respectively present the brand model, smoke flavor and electronic cigarette manufacturer in the code table. For example, a code segment that represents the brand model is AB, A refers that the code segment is related to the brand model, B is the brand model of the electronic cigarette, such as 'XX brand electronic cigarette'. A code segment representing the taste of the smoke liquid is CD, C indicates that the code segment is related to the taste of the smoke liquid, and D indicates that the smoke liquid taste of the electronic cigarette is 'XX taste'. A code segment representing the electronic cigarette manufacturer is EF, E indicates that the code segment is related to the electronic cigarette manufacturer, F refers that the electronic cigarette manufacturer is 'XX factory manufactured'. A, C, E are fixed sub-coding segments, and B, D, F are sub-coding segments encoded according to the specific circumstance of the electronic cigarette.

When the electronic cigarette receives the broadcast information, the code segment representing the electronic cigarette type in the broadcast information is compared with the code segment in the electronic cigarette's own code table. When a code segment in the code table is the same as the code segment representing the electronic cigarette type in the broadcast information, it is determined that the electronic cigarette sending the broadcast information is of the same type as the electronic cigarette that receives the broadcast information.

Certainly, the above function of sending the broadcast information is controllable, the electronic cigarette can turn off the function, and refuse to send the broadcast information. Thus, preferably, the method comprises following trigger step S01 before sending the broadcast information in the step S01:

S01. the electronic cigarette is triggered to produce a first trigger signal of activating a sending broadcast information function.

For example, a corresponding function switch is activated to send the first trigger signal. Certainly, it is understood that the first trigger signal may also be generated when the user inhales the electronic cigarette. For example, the first trigger signal may be generated when the electronic cigarette detects its own smoking signal. It is more convenient to use by sending the broadcast information when smoking, and, the smoke generated when smoking can also serve as a location indicator, it is easy for smokers having the same hobby to find each other, it provides a beneficial effect for the user experience.

Further, the electronic cigarette can also refuse to receive the broadcast information sent from the other electronic cigarettes to prevent information harassment, thus the method comprises following trigger step S02 before sending the broadcast information in the step S1:

S02. the electronic cigarette is triggered to produce a second trigger signal of activating a receiving broadcast information function.

For example, a corresponding function switch is activated to send the second trigger signal.

Preferably, the function switch comprises a first switch and a second switch, the first switch is configured for simultaneously sending a first trigger signal and a second trigger signal, and the second switch is configured for only sending the second trigger signal. The advantage of this control is that some users want to search for the existence of other electronic cigarettes, but do not want other electronic cigarettes to know their own existence, then they can only turn on the second switch. If the user agrees to let other electronic cigarette to find their own existence when searching for other electronic cigarettes at the same time, they can turn on the first switch. Certainly, the function switch can also be a switch that can sense different user actions, such as a multi-touch capacitive touch IC sensing a different touch path, or a single-touch capacitive touch IC sensing a long press, a short press, etc.

It is worth noting that the electronic cigarette receiving the broadcast information in step S2 receives at least one piece of the broadcast information, and the determining whether the electronic cigarette type carried by the broadcast information is same as the electronic cigarette's own electronic cigarette type in step S2 aims at respectively judging all of the broadcast information, the vibration alert also performs a vibration alert aims at a same type of electronic cigarette broadcast information.

However, there is a problem: the same electronic cigarette can repeatedly turns on the function of sending broadcast information for mischief. Therefore, in order to avoid such interference, each electronic cigarette includes a record table in which an electronic cigarette ID is recorded, and each time when receiving the broadcast information is activated, the electronic cigarette ID in the record table is cleared. The electronic cigarette ID in the present invention means that the electronic cigarette is different from a serial number of the other electronic cigarettes or a user name of the user who uses the electronic cigarette.

The broadcast information in the step S1 further carries the electronic cigarette ID configured to identify its own electronic cigarette;

In the step S2, if the electronic cigarette type carried by the broadcast information is determined to be same as the another electronic cigarette's own electronic cigarette type, it is first inquired whether the electronic cigarette ID carried by the broadcast information is in the record table, if not, then write the electronic cigarette ID carried by the broadcast information into the record table, and perform the vibration alert, otherwise, perform no response.

It can be seen, by adding the record table, the problem that the same electronic cigarette repeatedly turns on the function to send broadcast information for mischief can be effectively avoided.

Figure 2:
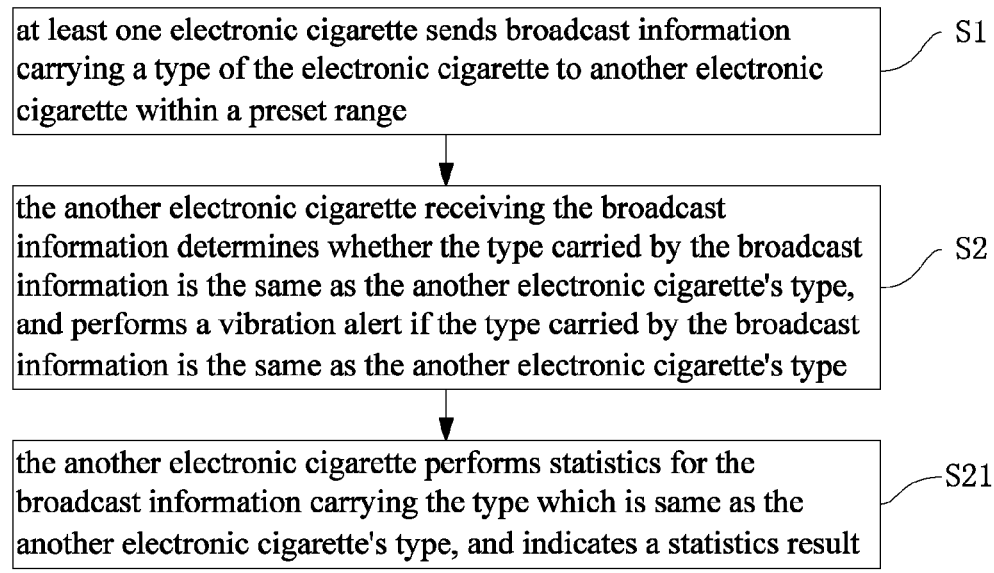
FIG. 2 is a flow chart of a second embodiment of the method for searching for an electronic cigarette of the same type of the present invention.

FIG. 2 is a flow chart of a second embodiment of the method for searching for an electronic cigarette of the same type of the present invention;

In order to facilitate the user to know the existence of around the same type of electronic cigarette enthusiasts around in the current time, preferably, on the basis of the first embodiment, the method further comprises after the step S2:

S21. perform statistics for the broadcast information which is obtained and carrying the electronic cigarette type which is same as the another electronic cigarette's own electronic cigarette type, and indicate a statistics result. For example, the statistics result in this embodiment is: a quantity of the broadcast information which is obtained and carrying the electronic cigarette type which is same as the another electronic cigarette's own electronic cigarette type.

Here, there are two ways to do statistics: one is to do statistics within a preset time, the other is to do real-time statistics.

Doing statistics within a preset time:

The preset time here means the preset time from when the user has turned on the function of receiving the broadcast information. That is, the broadcast information received in step S2 is substantially all of the broadcast information within a preset time. For example, once the electronic cigarette turns on the function switch to receive the broadcast information to search, then the function switch is turned on to start timing, and the number of statistics is cleared to zero, in the timing time, after the electronic cigarette determines the received broadcast information, if the electronic cigarette type carried by the broadcast information is same as its own, then the number of statistics value is added one, after the timing time reaches the preset time, the number of statistics will be prompted. At the same time if there are many enthusiasts of the same type of electronic cigarette, the information will be received in sequence. Thus, it is necessary to reserve a certain preset time for receiving and processing information. The preset time is generally set as a short, such as 10 s. For just wanting to know the quantity value of enthusiasts of the same type of electronic cigarette at this moment, this search is relatively simple and direct.

In this case, the vibration alert may be designed to be related to the above-mentioned quantity value, and specifically includes: the motor M performs several vibrations, there is a time interval between two adjacent vibrations, the number of vibration times of each vibration alert is same as the quantity. The advantage that the number of vibration times of each vibration alert is same as the quantity is, if a lot of the same type of electronic cigarettes are found, the vibration times correspondingly increases, on the contrary, fewer are found, the number of vibration is also smaller, giving a more direct induction.

Real-Time Statistics:

Real-time statistics is similar to online statistics, the real-time statistics conditions are, the broadcast information sent by the electronic cigarette also comprises its own electronic cigarette ID in order to facilitate the electronic cigarette receiving the broadcast information to send the confirmation information. Moreover, the electronic cigarette needs to store the broadcast information sent by the previous same type of electronic cigarette.

The process of the real-time statistics is:

On one hand, sending confirmation information to the electronic cigarette corresponding to each broadcast information in a certain time interval, the confirmation information is to confirm whether the other electronic cigarette is still within the preset range. If the other electronic cigarette is still within the preset range, then the confirmation information can be received, and response information is sent to inform the electronic cigarette sending the confirmation information. Thus, the number of response information received is the number of enthusiasts of the same type of electronic cigarette at this time. Certainly, the stored broadcast information is updated according to the received response information, and only the broadcast information sent by the electronic cigarette sending the response information is reserved.

On the other hand, as long as new broadcast information is received and it is determined that the type of the electronic cigarette carried is same as the type of the its own electronic cigarette type, the broadcast information is stored, and the statistical quantity value is updated to number of the new broadcast information plus previous statistical quantity value.

Although the statistical process of the real-time statistics is more complex, but can real-time online display number of the enthusiasts of the same type of electronic cigarette around, the user experience can be improved.

Indicating the quantity value comprises: a text display or/and a voice announcement.

Figure 3:
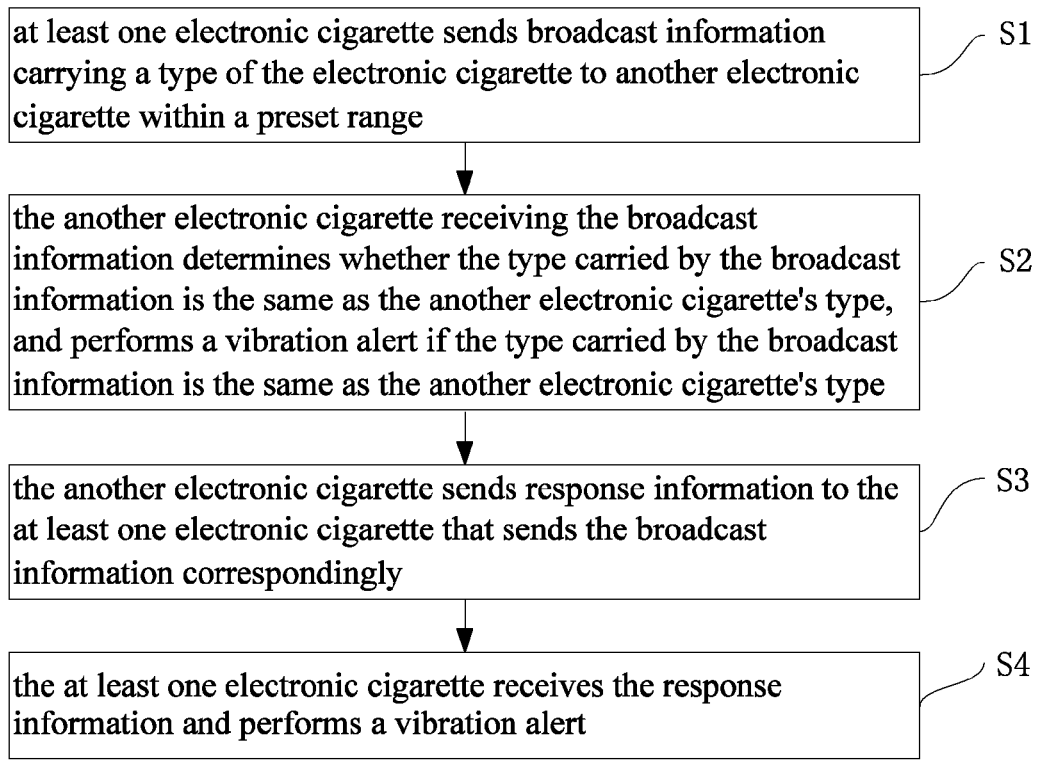
FIG. 3 is a flow chart of a third embodiment of the method for searching for an electronic cigarette of the same type of the present invention.

FIG. 3 is a flow chart of a third embodiment of the method for searching for an electronic cigarette of the same type of the present invention;

The same type of the electronic cigarette receiving the broadcast information in this embodiment can send response information to respond to the other for simple interaction.

Compared with the first embodiment, in the step S2, if the electronic cigarette type carried by the broadcast information is determined to be same as the another electronic cigarette's own electronic cigarette type, then at same time of performing the vibration alert, the method comprises:
  S3. send response information to the electronic cigarette that sends the corresponding broadcast information;
  S4. the electronic cigarette that receives the response information performs a vibration alert.

The vibration alert here should be separated from the vibration alert in above-mentioned step S2. For example, in the step S2, the existence of the same type of electronic cigarettes is indicated by several intermittent vibrations, a vibration that lasts a long time is used in the step S4, which not only represents the existence of the same type of electronic cigarettes, but also that the other gives a reply, strengthening the interaction and communication between electronic cigarettes. For example, when the response information is detected, the motor M vibrates continuously for 10 seconds without an interruption.

Preferably, the electronic cigarette performing the above-mentioned function of actively requesting others to reply the response information is also controllable.

Thus, if the user wants to interact with the same type of the electronic cigarette, a trigger step S03 is comprised before the step S2 sending the response information:
  S03. the electronic cigarette is triggered to produce a third trigger signal of activating a receiving broadcast information function.

Certainly, whether the other is willing to participate in interaction and receive the response information is controllable, the function of each electronic cigarette receiving the response information sent by other electronic cigarettes can be turned on and off via relevant function keys.

Figure 4:
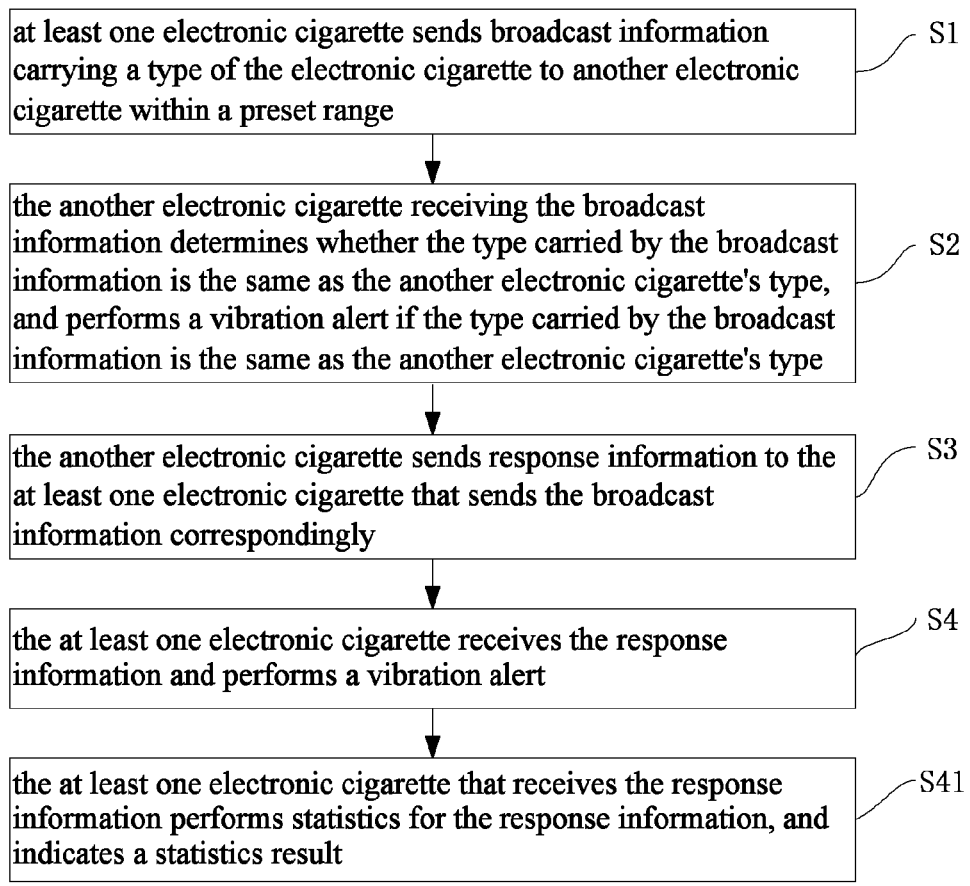
FIG. 4 is a flow chart of a fourth embodiment of the method for searching for an electronic cigarette of the same type of the present invention.

FIG. 4 is a flow chart of a fourth embodiment of the method for searching for an electronic cigarette of the same type of the present invention;

The fourth embodiment performs the statistical count for the replied corresponding information based on the third embodiment, and more specifically is:

After the step S4 the method comprises:
  S41. every electronic cigarette that receives the response information performs statistics for their own obtained response information, and indicates a statistics result.

Users can understand how many electronic cigarette users around have given their own interaction via the statistical indication. The difference between the statistical count here and the statistical count of the above-mentioned second embodiment is: receiving the broadcast information in the second embodiment is not controllable by a searcher, thus the above-mentioned methods of the real-time statistics and preset time statistics are proposed. In this embodiment, the response information is controlled by the searcher. Since the electronic cigarette that sends the response information is necessarily the electronic cigarette that receives the broadcast information sent by the searcher, the statistics is relatively simple.

Figure 5:
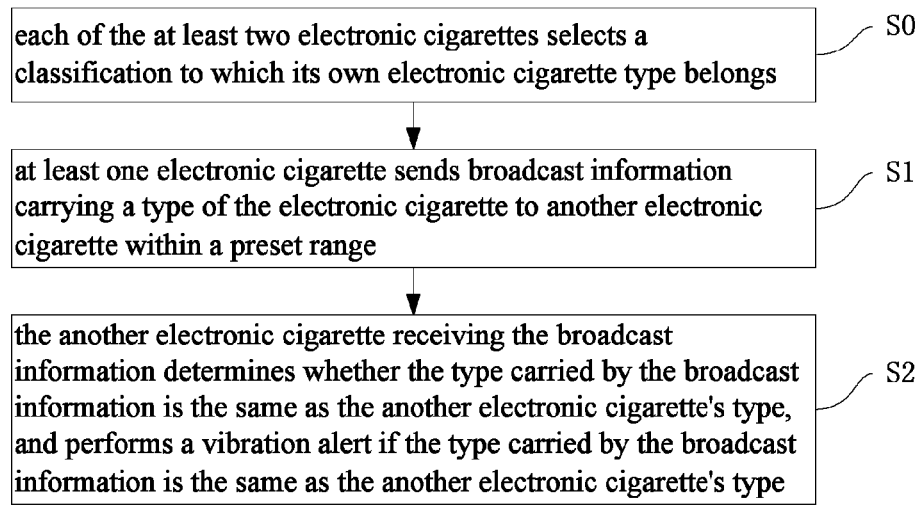
FIG. 5 is a flow chart of a fifth embodiment of the method for searching for an electronic cigarette of the same type of the present invention.

FIG. 5 is a flow chart of a fifth embodiment of the method for searching for an electronic cigarette of the same type of the present invention;

It is to be noted that the type of the electronic cigarettes in step S1 may be any classification representing the electronic cigarette information, for example, the electronic cigarette type belongs to one or more following classifications: a brand model, a smoke liquid taste, an electronic cigarette manufacturer.

The subordinate classification of the default electronic cigarette type is the brand model, certainly, in order to facilitate the user to select the type of electronic cigarette that needs to be searched, the subordinate electronic cigarette classifications are optional. That is, when users search for the same type, they can choose to search for the same brand model of electronic cigarettes, or the same smoke liquid taste of electronic cigarettes, or the same electronic cigarette manufacturers of electronic cigarettes.

Thus, in this embodiment, based on the first embodiment, before the step S1 the method comprises:
  S0. each electronic cigarette selects the classification to which its own electronic cigarette type belongs.

If the classification selected in step S0 is the smoke liquid taste, before step S1 the method further comprises:
  S11. detect the smoke liquid taste of the electronic cigarette.

For example, smoke liquid tastes comprise: chocolate smoke liquid, strawberry smoke liquid, coffee smoke liquid. If the classification selected by S0 is the smoke liquid taste, then the step S11 will detect the its own smoke liquid taste, and if it is the chocolate smoke liquid, the electronic cigarette loads the "chocolate smoke liquid" as its own electronic cigarette type into the broadcast information and sends out.

It can be understood that, in order to more clearly display the detailed information of the user's own electronic cigarette to other users, the electronic cigarette type in the broadcast information sent by the electronic cigarette can belong to at least two classifications, and as long as one classification is same, then it can be determined to be the same type of the electronic cigarette. Specifically, in the step S0, each electronic cigarette selects at least two classifications to which its own electronic cigarette type belongs; in this step, in order to facilitate the electronic cigarette receiving the broadcast information to divide the code segments representing each electronic cigarette type, the adjacent two code segments representing the electronic cigarette type are set to be empty, or set to be a predetermined special code segment.

In the step S2, performing the vibration alert comprises: vibrating times corresponding to the number of the same classifications to which the electronic cigarette belongs. In this embodiment, after the electronic cigarette receives the broadcast information, at least one code segment representing the electronic cigarette type in the broadcast information is respectively compared with the code segment in the own code table, and the quantity of the same code segment is counted, that is, the quantity of the same subordinate classification of the electronic cigarette is counted. Thus, the electronic cigarette user receiving the broadcast information can know not only there is a same type of electronic cigarette user around but also the similarity degree between the electronic cigarette smoke of the other user and the electronic cigarette of its own according to the vibration times of the motor, which can improve the user experience.

Figure 6:
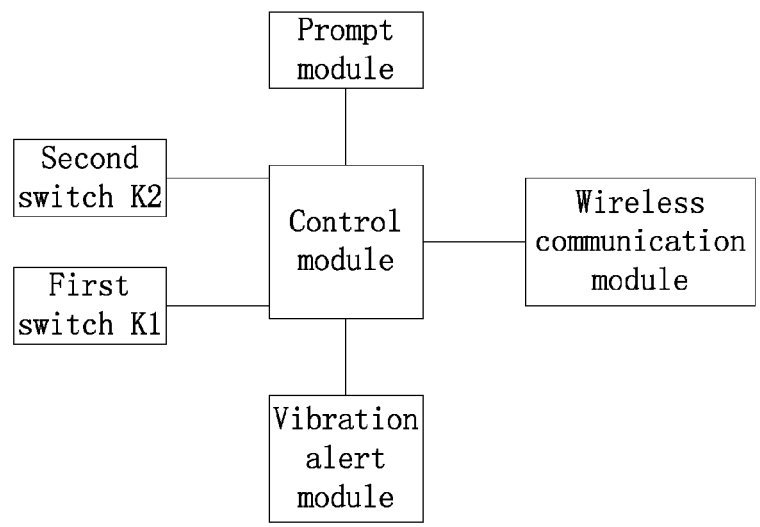
FIG. 6 is a structural diagram of the electronic cigarette in the system for searching an electronic cigarette of the same type of the present invention.

FIG. 6 is a structural diagram of the electronic cigarette in the system for searching an electronic cigarette of the same type of the present invention;

The electronic cigarette comprises: a control module, a wireless communication module, a vibration alert module, a prompt module, a first switch K1, and a second switch K2; the communication module, the vibration alert module, the prompt module, the first switch K1 and the second switch K2 are connected to the wireless communication module respectively;

The control module comprises a processor U1, the vibration alert module comprises a motor M and a driving circuit, the processor U1 stores a record table in which an electronic cigarette ID is recorded;

The first switch K1 is configured for simultaneously sending a first trigger signal and a second trigger signal, and the second switch K2 is configured for sending a second trigger signal; the first trigger signal is configured for activating a sending broadcast information function, the second trigger signal is configured for activating a receiving broadcast information function; referring to parts of the above method of the first embodiment, the first switch K1 is configured for simultaneously activating the function of sending and receiving the boast information; the second switch K2 is only configured for activating the function of receiving the boast information.

The control module is configured to load information of the electronic cigarette's own type into the wireless communication module after receiving the first trigger signal;

The wireless communication module is configured to send broadcast information carrying the electronic cigarette's own type to another electronic cigarette within a preset range; the wireless communication module is further configured to receive at least one piece of broadcast information sent by the another electronic cigarette and to send the broadcast information to the control module;

The control module is further configured to receive the broadcast information from the wireless communication module after receiving the second trigger signal, and determines whether the another electronic cigarette type carried in the broadcast information is same as the electronic cigarette's own electronic cigarette type, if the another electronic cigarette type carried by the broadcast information is the same as the electronic cigarette's own electronic cigarette type, then controls the vibration alert module to perform a vibration alert; the control module is also configured to performs statistics for the broadcast information that obtained carried the another electronic cigarette type is the same as the electronic cigarette's own electronic cigarette type;

The prompt module is configured to prompt the statistics result, such as a LCD text display, a voice announcement.

Figure 7:
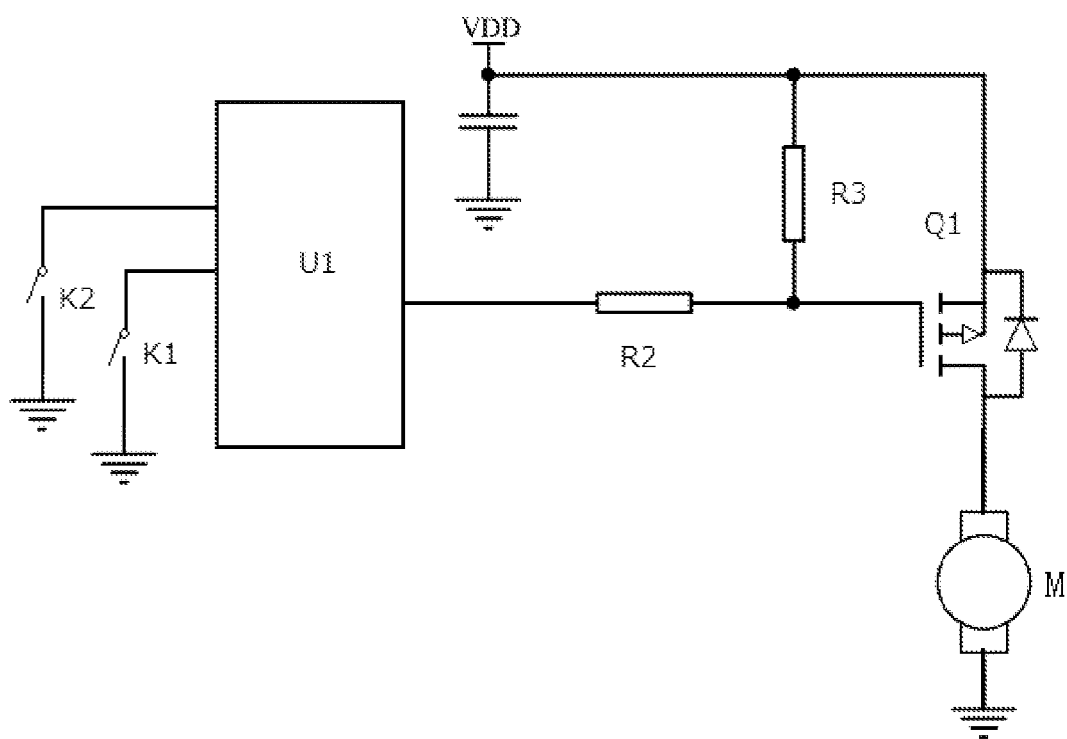
FIG. 7 is a circuit diagram of the vibration alert module in FIG. 6.

FIG. 7 is a circuit diagram of the vibration alert module in FIG. 6;

The control module comprises a TI AM335x ARM series processor U1, the vibration alert module comprises a motor M and a drive circuit, the drive circuit comprises an N-type MOS transistor Q1, a resistor R2 and a resistor R3; in this embodiment, the motor M is a conventional micro vibration motor.

A grid of the MOS transistor Q1 is connected to the processor U1 via the resistor R2, and the grid of the MOS transistor Q1 is also connected to a source of the MOS transistor Q1 via the resistor R3. The source of the MOS transistor Q1 is connected to an internal power supply VDD, and a drain of the MOS transistor Q1 is connected to a power supply interface of the motor M.

Normally, the processor U1 outputs a low level to the gird of the MOS transistor Q1, so that the MOS transistor Q1 is cut off and the motor M stops and does not vibrate. The control module controls the vibration reminder module to vibrate specifically: the processor U1 outputs a high level to the grid of the MOS transistor Q1, and the MOS transistor Q1 conducts, and the motor M is energized and vibrates.

Figure 8:
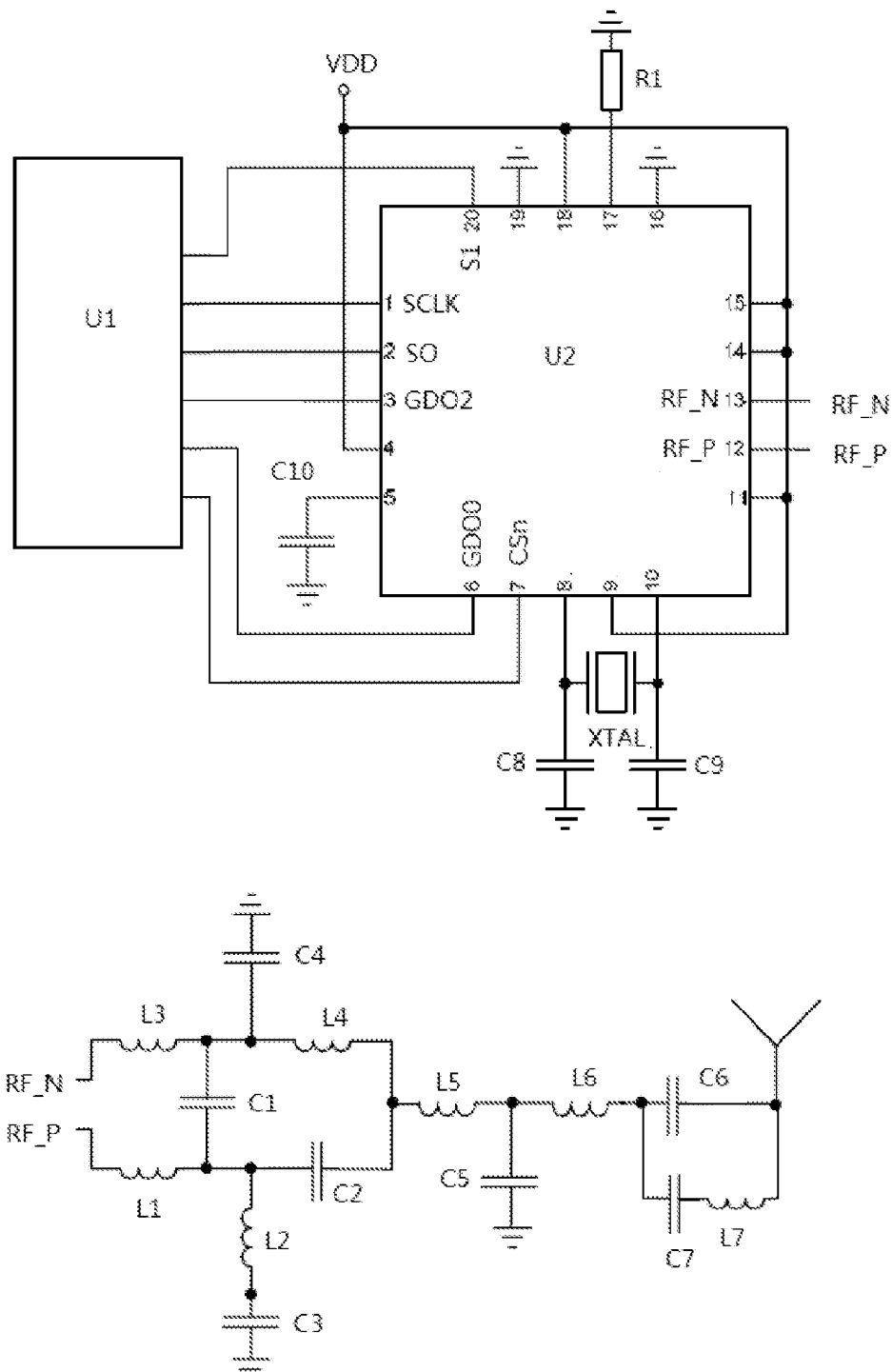
FIG. 8 is a circuit diagram of the wireless communication module in FIG. 6.

FIG. 8 is a circuit diagram of the wireless communication module in FIG. 6.

In the preferred embodiment, the wireless communication module comprises a CC1101 wireless transceiver chip U2, which can transmit during a range of a distance of 300-500 meters.

A RF_N pin of the wireless transceiver chip U2 is connected to a first end of an inductor L5 via an inductance L3 and an inductance L4. A RF_P pin is connected to the first end of the inductor L5 via an inductor L1 and a capacitor C2, and the connected node of the inductance L3 and inductance L4 is grounded via a capacitor C4, and the connected node of the inductor L1 and the capacitor C2 is grounded via the inductor L2 and a capacitor C3. The second end of the inductor L5 is connected to an antenna via a inductor L6 and a capacitor C6. The connected node of the inductor L5 and the inductor L6 is grounded via a capacitor C5, a capacitor C7 and a inductor L7 are in series and then in parallel with the capacitor C6.

A SCLK pin, a CSn pin and a S1 pin of the wireless transceiver chip U2 are respectively connected to the corresponding pins of the processor U1, and are respectively configured to receive a time signal, a chip select signal and a data which are outputted by the processor U1.

A SO pin or a GDO1 pin, a GDO2 pin, and a GDO0 pin of the wireless transceiver chip U2 are connected to the corresponding pins of the processor U1. When the CSn pin receives a high level, the SO pin outputs data to the processor U1.

It is to be noted that the specific components in the wireless communication module, and their models and connection relationships are not limited here. The wireless communication module may also be a wifi module, a Bluetooth module, etc., or a module for radio-frequency communication using frequencies such as 315 MHz, 433 MHz, or 900 MHz, which are within the protected scope of the present invention.

The sixth embodiment of the system for searching for an electronic cigarette of same type comprises:
- S0. each electronic cigarette selects a classification to which its own electronic cigarette type belongs;
  the electronic cigarette type belongs to one or more following classifications: a brand model, a smoke liquid taste, an electronic cigarette manufacturer;
- S01. the first switch K1 of the electronic cigarette is triggered to generate the first trigger signal;
- S1. the wireless communication module of the electronic cigarette in the step S01 sends broadcast information carrying the electronic cigarette ID for identifying its own electronic cigarette and an electronic cigarettes' own electronic cigarette type to another electronic cigarette in a preset range;
- S02. the first switch K1 or the second switch K2 of the another electronic cigarette is triggered to generate the second trigger signal;
- S2. the wireless communication module of the another electronic cigarette receiving the broadcast information in the step S02 sends the broadcast information to the processor U1, the processor U1 determines whether the electronic cigarette type carried by the broadcast information is the same as the another electronic cigarette's own electronic cigarette type, and if the electronic cigarette type carried by the broadcast information is the same as the another electronic cigarette's own electronic cigarette type, it is first inquired whether the electronic cigarette ID carried in the broadcast information exists in the record table, if not, write the electronic ID carried by the broadcast information into the record table, and control the driving circuit to drive the motor M to perform a vibration alert, otherwise, perform no response;
- S21. the processor U1 of the another electronic cigarette receiving the broadcast information performs statistics for the broadcast information which is obtained and carrying the electronic cigarette type which is the same as the another electronic cigarette's own electronic cigarette type, and carries out a text display and/or a voice announcement via the prompt module; the statistics result comprises: a quantity of the broadcast information which is obtained and carrying the electronic cigarette type which is the same as the another electronic cigarette's own electronic cigarette type;

The controlling the driving circuit to drive the motor M to perform the vibration alert comprises: the driving circuit drives the motor M to vibrate several times, there is a time interval between two adjacent vibrations, a number of vibration times of each vibration alert is same as the quantity.

In summary, each electronic cigarette of the present invention can send the broadcast information carrying the electronic cigarette's own electronic cigarette type to another electronic cigarette in the preset range, after the another electronic cigarette receives at least one piece of the broadcast information, it is determined whether the type of the electronic cigarette carried by the broadcast information is the same as the another electronic cigarette's own electronic cigarette type, if the type of the electronic cigarette carried by the broadcast information is the same as the another electronic cigarette's own electronic cigarette type, then it is determined there are enthusiasts of the same type electronic cigarette around, then the electronic cigarette receiving the broadcast information can be controlled to perform a vibration alert, and quickly learn whether there are electronic cigarette users around that use the same electronic cigarette to find enthusiasts of the same type electronic cigarette, making electronic cigarettes no longer a separate individual, and to enhance the user experience, so that users know more about what type of electronic cigarette is better, which will promote the popularization of electronic cigarettes, and further facilitate quitting smoking, in order to achieve universal health of smoking.

Combining with the accompanying drawings, embodiments of the present invention are described. However, the present invention is not limited by the above embodiments, which means that the above specific embodiments are only schematic, rather than restrictive. It should be understood that, in the inspiration of the present invention, those skilled in the art who appreciate and realize all or part of the process in above embodiments may make many modifications or alternatives, without going beyond the purpose and the scope the claims intend to protect of the present application. All these belong to the protection of the present invention.

What claimed is:

1. A method for searching for an electronic cigarette of a same type, the method comprises at least two electronic cigarettes performing a communication connection, wherein the method comprises the following steps:
   - S1: at least one electronic cigarette sends broadcast information carrying a type of the electronic cigarette to another electronic cigarette within a preset range;
   - S2: the another electronic cigarette receiving the broadcast information determines whether the type carried by the broadcast information is the same as the another electronic cigarette's type, and performs a vibration alert if the type carried by the broadcast information is the same as the another electronic cigarette's type;
   - S21: the another electronic cigarette performs statistics for the broadcast information carrying the type which is same as the another electronic cigarette's type, and indicates a statistics result; and
   wherein the statistics result comprises: a quantity of received broadcast information carrying the type which is same as the another electronic cigarette's type,
   the vibration alert comprises: a motor vibrates several times, there is a time interval between two adjacent vibrations, a number of vibration times of every vibration is same as the quantity.

2. The method for searching for an electronic cigarette of a same type according to claim 1, wherein each of the at least two electronic cigarettes comprises a record table for recording electronic cigarette ID;
   the broadcast information sent by the at least one electronic cigarette in the step S1 further carries its own electronic cigarette ID configured to identify the at least one electronic cigarette;
   in the step S2, if the type carried by the broadcast information is determined to be the same as the another electronic cigarette's type, the another electronic cigarette firstly inquires whether the electronic cigarette ID carried by the broadcast information is in its record table, if not, writes the electronic cigarette ID carried by the broadcast information into the record table, and performs the vibration alert, otherwise, performs no response.

3. The method for searching for an electronic cigarette of a same type according to claim 1, wherein the method comprises a following trigger step S01 before sending the broadcast information in the step S1:
S01: each of the at least two electronic cigarettes is triggered to produce a first trigger signal of activating a sending broadcast information function.

4. The method for searching for an electronic cigarette of a same type according to claim 3, wherein in the step S01, the each of the at least two electronic cigarettes produces the first trigger signal of activating the sending broadcast information function when the each of the at least two electronic cigarettes detects its own smoking signal.

5. The method for searching for an electronic cigarette of a same type according to claim 1, wherein the method comprises a following trigger step S02 before sending the broadcast information in the step S1:
S02: each of the at least two electronic cigarettes is triggered to produce a second trigger signal of activating a receiving broadcast information function.

6. The method for searching for an electronic cigarette of a same type according to claim 1, wherein in the step S2, if the type carried by the broadcast information is determined to be same as the another electronic cigarette's type, then the another electronic cigarette performs the vibration alert, at same time the method further comprises:
S3: the another electronic cigarette sends response information to the at least one electronic cigarette that sends the broadcast information correspondingly;
S4: the at least one electronic cigarette receives the response information and performs a vibration alert.

7. The method for searching for an electronic cigarette of a same type according to claim 6, wherein after the step S4, the method further comprises:
S41: the at least one electronic cigarette that receives the response information performs statistics for the response information, and indicates a statistics result.

8. The method for searching for an electronic cigarette of a same type according to claim 1, wherein the at least two electronic cigarette types belong to one or more following classifications: a brand model, a smoke liquid taste, an electronic cigarette manufacturer.

9. The method for searching for an electronic cigarette of a same type according to claim 8, wherein before the step S1, the method further comprises:
S0: each of the at least two electronic cigarettes selects a classification to which its own electronic cigarette type belongs.

10. The method for searching for an electronic cigarette of a same type according to claim 9, wherein in the step S0, each of the at least two electronic cigarettes selects at least two classifications to which its own electronic cigarette type belongs;
in the step S2, the another electronic cigarette performing the vibration alert comprises: vibrates times corresponding to a number of the same classifications to which the type belongs.

11. The method for searching for an electronic cigarette of a same type according to claim 1, wherein in the step S21, indicating the statistics result comprises: a text display or/and a voice announcement.

12. A method for searching for an electronic cigarette of a same type, the method comprises at least two electronic cigarettes performing a communication connection, wherein each of the at least two electronic cigarettes comprises: a control module, a wireless communication module, a vibration alert module, a prompt module, a first switch (K1), and a second switch (K2); the wireless communication module, the vibration alert module, the prompt module, the first switch (K1) and the second switch (K2) are connected to the control module respectively;
the control module comprises a processor (U1),
the vibration alert module comprises a motor (M) and a driving circuit, the processor (U1) stores a record table for recording electronic cigarette ID;
the first switch (K1) is configured for simultaneously sending a first trigger signal and a second trigger signal, and the second switch (K2) is configured for sending the second trigger signal; the first trigger signal is configured for activating a sending broadcast information function, the second trigger signal is configured for activating a receiving broadcast information function;
the method comprises following steps:
S0: the each of the at least two electronic cigarettes selects a classification to which its own electronic cigarette type belongs;
the electronic cigarette type belongs to one or more following classifications: a brand model, a smoke liquid taste, an electronic cigarette manufacturer;
S01: the first switch (K1) of at least one electronic cigarette is triggered to generate the first trigger signal;
S1: the wireless communication module of the at least one electronic cigarette in the step S01 sends broadcast information carrying electronic cigarette ID for identifying its own electronic cigarette and a type of the at least one electronic cigarette type to another electronic cigarette in a preset range;
S02: the first switch (K1) or the second switch (K2) of the another electronic cigarette is triggered to generate the second trigger signal;
S2: the wireless communication module of the another electronic cigarette receiving the broadcast information in the step S02 sends the broadcast information to the processor (U1), the processor (U1) determines whether the type carried by the broadcast information is the same as the another electronic cigarette's type, and if the type carried by the broadcast information is the same as the another electronic cigarette's type, firstly inquires whether the electronic cigarette ID carried by the broadcast information exists in its record table, if not, writes the electronic cigarette ID carried by the broadcast information into the record table, and controls the driving circuit to drive the motor (M) to perform a vibration alert, otherwise, performs no response;
S21: the processor (U1) of the another electronic cigarette receiving the broadcast information performs statistics for the broadcast information carrying the electronic cigarette type which is the same as the another electronic cigarette's type, and carries out a text display and/or a voice announcement via the prompt module; a statistics result comprises: a quantity of the broadcast information carrying the type which is the same as the another electronic cigarette's type;
wherein controlling the driving circuit to drive the motor (M) to perform the vibration alert comprises: the driving circuit drives the motor (M) to vibrate several times, there is a time interval between two adjacent vibrations, a number of vibration times of each vibration alert is same as the quantity.

13. A system for searching for an electronic cigarette of a same type, the system comprises at least two electronic cigarettes, wherein each of the at least two electronic cigarette comprises:
a control module, a wireless communication module, a vibration alert module, a prompt module, a first switch (K1), and a second switch (K2); the wireless communication module, the vibration alert module, the prompt module, the first switch (K1) and the second switch (K2) are connected to the control module respectively;
the control module comprises a processor (U1), the vibration alert module comprises a motor (M) and a driving circuit, the processor (U1) stores a record table for recording electronic cigarette ID;
the first switch (K1) is configured for simultaneously sending a first trigger signal and a second trigger signal, and the second switch (K2) is configured for sending the second trigger signal; the first trigger signal is configured for activating a sending broadcast information function, the second trigger signal is configured for activating a receiving broadcast information function;
the control module of at least one electronic cigarette is configured to load information of an type of the at least one electronic cigarette into the wireless communication module of the at least one electronic cigarette after receiving the first trigger signal;
the wireless communication module of the at least one electronic cigarette is configured to send broadcast information carrying the type of the at least one electronic cigarette to another electronic cigarette within a preset range; the wireless communication module of the at least one electronic cigarette is further configured to receive at least one broadcast information sent by the another electronic cigarette and to send the received broadcast information to the control module of the at least one electronic cigarette;
the control module of the at least one electronic cigarette is further configured to obtain the received broadcast information from the wireless communication module of the at least one electronic cigarette after receiving the second trigger signal, and to determine whether another electronic cigarette type carried by the received broadcast information is the same as the type of the at least one electronic cigarette, if the another electronic cigarette type carried by the received broadcast information is the same as the type of the at least one electronic cigarette, then to control the vibration alert module to perform a vibration alert; the control module of the at least one electronic cigarette is also configured to perform statistics for the received broadcast information carrying the another electronic cigarette type which is same as the type of the at least one electronic cigarette;
the prompt module is configured to prompt a statistics result.

* * * * *